United States Patent [19]

Kimble et al.

[11] Patent Number: 4,620,057

[45] Date of Patent: Oct. 28, 1986

[54] METHANE CONVERSION

[75] Inventors: James B. Kimble, Bartlesville; John H. Kolts, Ochelata, both of Okla.

[73] Assignee: Phillips Petroleum Company, Bartlesville, Okla.

[21] Appl. No.: 742,339

[22] Filed: Jun. 7, 1985

[51] Int. Cl.[4] .............................................. C07C 2/00
[52] U.S. Cl. ............................. 585/500; 585/415; 585/417; 585/418; 585/541; 585/654; 585/656; 585/657; 585/658; 585/661; 585/700; 585/943
[58] Field of Search ............... 585/400, 415, 417, 418, 585/500, 541, 654, 656, 657, 658, 661, 700, 943

[56] References Cited

U.S. PATENT DOCUMENTS

| | | | |
|---|---|---|---|
| 1,863,212 | 6/1932 | Winkler | 585/415 |
| 3,810,953 | 5/1974 | Cichowski | 585/658 |
| 3,845,156 | 10/1974 | Farka | 585/658 |
| 4,205,194 | 5/1980 | Mitchell, III et al. | 585/407 |
| 4,239,658 | 12/1980 | Mitchell, III et al. | 585/943 |
| 4,368,346 | 1/1983 | Eastman | 585/658 |
| 4,396,537 | 8/1983 | Eastman | 502/213 |
| 4,443,644 | 4/1984 | Jones et al. | 585/500 |
| 4,443,645 | 4/1984 | Jones et al. | 585/500 |
| 4,443,646 | 4/1984 | Jones et al. | 585/500 |
| 4,443,648 | 4/1984 | Jones et al. | 585/500 |
| 4,443,649 | 4/1984 | Jones et al. | 585/500 |
| 4,444,984 | 4/1984 | Jones et al. | 585/500 |
| 4,450,310 | 5/1984 | Fox et al. | 585/500 |
| 4,465,893 | 8/1984 | Olah | 585/943 |
| 4,497,970 | 2/1985 | Young | 585/417 |
| 4,497,971 | 2/1985 | Eastman et al. | 585/658 |
| 4,523,049 | 6/1985 | Jones et al. | 585/500 |
| 4,523,050 | 6/1985 | Jones et al. | 585/415 |

FOREIGN PATENT DOCUMENTS

3237079  4/1984  Fed. Rep. of Germany .

OTHER PUBLICATIONS

Hinsen, Bytyn and Baerns, Oxidative Dehydrogenation and Coupling of Methane, 8th Int. Congress on Catalysis.
Keller and Bhasen, "Synthesis of Ethylene via Oxidative Coupling of Methane", J. of Catalysis, 73, 9–19 (1982).
Hinsen and Baerns, "Oxidative Koppling von Methan Zu$C_2$-Kohlenuasserstuffen in Gegenwark unterschulalicher Katalysatinen, "Chemical Zeiting" vol. 167, No. 708, 1983.
Fang and Yeh, "Catalytic Pyrolysis of Methane," J of Chinese Chemical Society, 29, 265–273 (1981).

*Primary Examiner*—William R. Dixon, Jr.
*Assistant Examiner*—Cynthia A. Prezlock
*Attorney, Agent, or Firm*—Charles F. Steininger

[57] ABSTRACT

A method for the oxidative conversion of a feed material comprising methane, such as natural gas, to higher hydrocarbons, particularly ethylene and ethane and desirably ethylene, in which feed is contacted with a solid contact material comprising cobalt; at least one metal selected from the group consisting of zirconium, zinc, niobium, indium, lead and bismuth, preferably, zirconium; phosphorous; at least one Group IA metal; and oxygen under oxidative conversion conditions sufficient to convert the methane to the higher hydrocarbons. Substantial improvement in the conversion of methane and selectivity to ethylene and ethane is obtained by adding chlorine to the contact material. The further addition of sulfur to the contact material also improves the conversion and selectivity and permits the method to be carried out in an essentially continuous manner in the presence of a free oxygen containing gas.

20 Claims, No Drawings

METHANE CONVERSION

The present invention relates to methane conversion. In a more specific aspect, the present invention relates to methane conversion to higher hydrocarbons. In a still more specific aspect, the present invention relates to methane conversion to ethylene and ethane.

BACKGROUND OF THE INVENTION

Olefins, such as ethylene and propylene, have become major feedstocks in the organic chemical and petrochemical industries. Of these, ethylene is by far the more important chemical feedstock, since the requirements for ethylene feedstocks are about double those for propylene feedstocks. Consequently, feedstocks for the production of ethylene are in relatively short supply.

Numerous suggestions have been made for the production of ethylene from various feedstocks by a variety of processes.

At the present time, ethylene is produced almost exclusively by dehydrogenation or pyrolysis of ethane and propane, naptha and, in some instances, gas oils. About 75% of the ethylene is produced by steam cracking of ethane and propane derived from natural gas. However, natural gas contains as little as 5 volume percent and, in rare instances, as much as 60 volume percent of hydrocarbons other than methane, the majority of which is ethane. However, typical natural gases contain less than about 12 to 15% of ethane. In addition to the relatively small quantities of ethane and propane available for use, separation of these components from natural gas is itself an expensive and complex process, usually involving compression and expansion, cryogenic techniques and combinations thereof.

It would, therefore, be highly desirable to be able to produce ethylene from the much more abundant methane. However, methane's high molecular stability, compared to other aliphatics, makes its use in ethylene production difficult and no significant amount of ethylene is produced commercially from methane at the present time.

Pyrolytic or dehydrogenative conversion of methane or natural gas to higher hydrocarbons has been proposed. However, relatively severe conditions, particularly temperatures in excess of 1000° C., are required. In addition, such reactions are highly endothermic and thus energy intensive. In order to reduce the severity of the conditions, particularly temperature, numerous proposals to catalyze pyrolytic reactions have been made. Some of these processes do, in fact, reduce the required temperatures, but the conversion of methane and the selectivity to ethylene are still quite low.

Another promising approach is the oxidative conversion of methane or natural gas to higher hydrocarbons. However, these techniques are still in the developmental stage and experimentation is hampered by differences of opinion and lack of a complete understanding of the process. For example, most workers in the art refer to the process as "oxidative coupling". However, there is little agreement with regard to the function performed by the oxygen and how this function is performed. Accordingly, the terminology, "oxidative coupling", will be avoided herein, and the present process, irrespective of the function of the oxygen or of the manner in which it performs its function, will be referred to as "oxidative conversion of methane". In such processes, it is conventional to contact the methane with solid materials. The nature of these contact materials, the function thereof and the manner in which such function is performed are also subject to diverse theories. For example, workers in the art refer to the function of the contact material as a purely physical phenomenon, in some cases as adsorption-desorption either of atomic or molecular oxygen and either on the surface or occluded within the solid material, oxidation-reduction utilizing multivalent metals capable of oxidation-reduction, adsorption and desorption of the hydrocarbons on the solid materials, a free radical mechanism, etc. Consequently, the solid materials, utilized in the process, are referred to as "contact materials", "promoters", "activators" and "catalysts". Accordingly, in order to avoid functional categorization, the terms "solid contact material" or "solid contact materials" will be utilized in the present application.

Based on the prior art, oxidative conversion of methane results in the formation of a variety of products. The most readily produced products are carbon dioxide, carbon monoxide and/or water and methanol, formaldehyde and other oxygenated hydrocarbons in combination with one or more of carbon dioxide, carbon monoxide and water. Higher hydrocarbons, particularly ethylene and ethane, are either not formed or are formed in such small quantitites that commercially viable processes have not been developed to date. Along with poor selectivity to higher hydrocarbons, particularly ethylene and ethane and still more particularly to ethylene, such processes also result in low conversions of the methane feed.

It is clear from the above that the suitability of particular contact materials is unpredictable. In addition to being dependent upon the type of contact material, the conversion of methane and selectivity to particular products also depends upon the conditions and the manner in which the reaction is carried out, and there is also little basis for predicting what conditions or what mode of operation will result in high conversions and selectivity to particular products.

SUMMARY OF THE INVENTION

It is therefore, an object of the present invention to provide an improved method for the conversion of methane. Another and further object is to provide an improved method for the oxidative conversion of methane. Yet another object is to provide a method for the oxidative conversion of methane at improved conversion levels. Another and further object of the present invention is to provide a method for the oxidative conversion of methane, which results in improved selectivity to higher hydrocarbons. A further object of the present invention is to provide a method for the oxidative conversion of methane, which results in improved conversion and selectivity to higher hydrocarbons. A still further object of the present invention is to provide a method for the oxidative conversion of methane, which results in improved selectivity to ethylene and ethane. Yet another object of the present invention is to provide a method for the oxidative conversion of methane, which results in improved conversion and selectivity to ethylene and ethane. Another object of the present invention is to provide a method for the oxidative conversion of methane, which results in improved selectivity to ethylene. Another and further object of the present invention is to provide a method for the oxidative conversion of methane, which results in improved conversion and selectivity to ethylene. A further object of the present invention is to provide a method for the oxidative conversion of methane, which can be carried out utilizing inexpensive starting materials. Another object of the present invention is to provide a method for the oxidative conversion of methane, which can be carried out under relatively mild conditions. A still further object of the present invention is to provide a method for the oxidative conversion of methane utilizing an improved contact material.

These and other objects and advantages of the present invention will be apparent from the following description.

In accordance with the present invention it has been found that methane can be converted to higher hydrocarbons, particularly ethylene and ethane, by:

contacting a feed material comprising methane with a solid contact material, comprising:

cobalt; at least one metal selected from the group consisting of zirconium, zinc, niobium, indium, lead and bismuth; phosphorous; at least Group IA metal; oxygen, and, optionally, a material selected from the group consisting of a halogen and sulfur;

under oxidative conversion conditions sufficient to convert said methane to said higher hydrocarbons.

Substantially improved conversion of methane and selectivity to higher hydrocarbons, particularly ethylene and ethane, is obtained by the addition of a halogen, preferably chlorine.

The method can be carried out in a cyclic manner (methane conversion, preferably followed by a purge with an inert gas, such as nitrogen, and regeneration by contact with a free oxygen containing gas). However, the further addition of sulfur to the contact material not only increases conversion of methane and selectivity to higher hydrocarbons, particularly ethylene and ethane, but permits the method to be carried out in a continuous manner (by contacting a methane-containing gas and a free oxygen containing gas with the contact material).

Zirconium is a preferred metal from the group consisting of zirconium, zinc, niobium, indium, lead and bismuth. The preferred Group IA metal is sodium. However, the addition of a second Group IA metal, preferably potassium, improves results under certain operating conditions.

DETAILED DESCRIPTION

In accordance with the present invention, it has been found that substantially improved conversion of methane to higher hydrocarbons can be obtained by the oxidative conversion of methane to produce higher hydrocarbons at substantially improved selectivities, particularly to ethylene and ethane, by:

contacting a methane-containg gas with a solid contact material, comprising:

cobalt; at least one metal selected from the group consisting of zirconium, zinc, niobium, indium, lead and bismuth; phosphorous; at least one Group IA metal; oxygen, and, optionally, at least one material selected from the group consisting of a halogen and sulfur, under oxidative conversion conditions sufficient to convert the methane to higher hydrocarbons, particularly ethylene and ethane.

A preferred metal from the group consisting of zirconium, zinc, niobium, indium, lead and bismuth is zirconium. A preferred Group IA metal is sodium, resulting in the following combination:

Co/Zr/P/Na/O

While the above contact material is capable of converting methane to higher hydrocarbons, particularly ethylene and ethane, the conversion and selectivity are relatively poor. However, the addition of a halogen, such as chlorine, to this composition substantially improves both the conversion of methane and the selectivity to higher hydrocarbons, particularly ethylene and ethane. The chlorine can be added to the contact material during its preparation, thus resulting in the following contact material:

Co/Zr/P/Na/Cl/O or by pretreating the contact material with a halogen-containing gas in the reactor prior to conduct of the reaction, as will be detailed hereinafter in the description of the preparation of the contact material and the methods of operation.

In accordance with most previous theories of the function and operation of contact materials for the oxidative conversion of methane to higher hydrocarbons, particularly ethylene and ethane, the reaction has been carried out in the absence of a free oxygen containing gas, with the oxygen theoretically being supplied by the contact material. As a result, the most utilized modes of operation have included treating the contact material with a free oxygen containing gas, such as oxygen or air, for a period of time sufficient to produce a reducible oxide of a multivalent metal, thereafter, contacting methane with the reducible metal oxide and, thereafter, treating the reduced metal oxide with a free oxygen containing gas to "regenerate" the same. Similarly, certain contact materials are contacted with a free oxygen containing gas to cause adsorption of oxygen on the contact material, methane is, thereafter, contacted with the contact material containing adsorbed oxygen and, thereafter, the contact material is again treated with a free oxygen containing gas. In both instances, the contact material, after treatment with a free oxygen containing gas, is purged with an inert gas, such as nitrogen, to remove excess oxygen which has not reacted with or been adsorbed on the contact material. Consequently, several techniques have been followed, including, carrying out the contact with methane and the contact with a free oxygen containing gas in separate reaction chambers or sequentially passing a free oxygen containing gas, a purge gas and methane through the contact material in a single reaction vessel. The disadvantages of either of these procedures will be evident to one skilled in the art.

The method of the present invention can be carried out in a cyclic manner as set forth above. For example, the methane feed can be passed through a fixed bed of the contact material until such time as the conversion and/or selectivity reach an unacceptable point. Flow of feed methane is then discontinued and the catalyst is purged with an inert gas, such as nitrogen. Following this purge, a free oxygen containing gas, such as air, is passed therethrough to regenerate the contact material. This cycle is then repeated. Some of the problems with such a cyclic operation are pointed out above and these and others are well known to those skilled in the art.

It has been found that the method can be carried out in an essentially continuous manner while at the same time further increasing both the conversion of methane and the selectivity to higher hydrocarbons, particularly ethylene and ethane, by the further addition of sulfur to the contact material. This will result in the following contact material:

Co/Zr/S/P/Na/Cl/O

A brief example of such an operation involves passing a methane-containing gas and a free oxygen containing gas over the above mentioned contact material. When utilizing this contact material and carrying out the method in an essentially continuous manner, it has been found that the contact material maintains its conversion and selectivity abilities for extended periods of time without further treatment of the contact material or regeneration. However, should such further treatment or regeneration be necessary or desirable, this contact material can also be treated or regenerated periodically as detailed hereinafter.

While the preferred alkali metal is sodium, as set forth above, it is also desirable to include a second Group IA metal, particularly potassium, thereby resulting in the following contact material:

Co/Zr/S/P/Na/K/Cl/O

The inclusion of potassium in the contact material has some effect on the conversion of methane and selectivity to higher hydrocarbons but can be eliminated. However, the presence or absence of potassium is significant if a particular method of forming the contact material and operating the process is followed. Specifically, if a halogen, particularly chlorine, is included in the catalyst, which of course is necessary for best results, the presence or absence of potassium is not a significant factor. However, if the contact material is prepared without the halogen, the halogen may be added by pretreating the contact material with a halogen-containing gas, such as methyl chloride, and, thereafter, passing the feed over the contact material for the reaction. In this case, the presence or absence of potassium is not too significant. However, if the contact material is prepared without the halogen and a gas containing halogen is co-fed with the feed material, during the reaction, in an effort to supply the halogen, then the presence of potassium in the contact material appears necessary.

In addition to methane, the hydrocarbon feedstock, employed in the method of the present invention, may contain other hydrocarbon or non-hydrocarbon components. The presence of ethane, propane and the like is not detrimental. It has been found that carbon dioxide and water are not detrimental, since they are often products of the process. It has also been found that inert gases, such as nitrogen, helium and the like are not detrimental. Consequently, the method of the present invention can effectively utilize any conventional natural gas.

The free oxygen containing gas may be any suitable oxygen containing gas, such as oxygen, oxygen-enriched air or air. The method of the present application has been effectively carried out utilizing air as a source of oxygen.

When utilized in the present invention, the term "diluent gas" is meant to include any gaseous material, present in the methane-containing gas, the free oxygen containing gas or in the form of an added gas, which is essentially inert with respect to the oxidative conversion of methane and, thus, does not significantly decrease the conversion of methane and/or the selectivity to the production of higher hydrocarbons.

As previously pointed out, certain of the components of the contact material are an absolute necessity (cobalt, a metal selected from the Group consisting of zirconium, zinc, niobium, indium, lead and bismuth, phosphorous, at least one Group IA metal and oxygen). A halogen is necessary in order to attain acceptable conversion and selectivity. The sulfur is necessary to permit essentially continuous operation of the method. A second Group IA metal, such as potassium, is desirable. However, the relative proportions of the components does not appear to be particularly critical. Accordingly, any amounts of the individual components may be present so long as effective amounts of the other components are present. The term "effective amount" is used herein to identify the quantity of the component which, when present in the contact material, results in a significant increase in the conversion of methane and/or the selectivity to higher hydrocarbons, particularly ethylene and ethane, compared with a contact material without the component in question. Preferably, however, the cobalt and the metal selected from the group consisting of zirconium, zinc, niobium, indium, lead and bismuth are utilized as major components while the remaining components are utilized in minor amounts. By way of example, the preferable atomic ratio of cobalt to the metal selected from the group consisting of zirconium, zinc, niobium, indium, lead and bismuth is in the range of about 1/1 to about 20/1 and more preferably in the range of about 3/1 to about 6/1. The phosphorous is preferably present in an amount of about 1 wt. percent to about 10 wt. percent and more preferably between about 2 wt. percent and about 5 wt. percent, expressed in terms of phosphorous oxide based on the total weight of the contact material. Preferably, the alkali metal is present in concentrations of about 1 wt. percent to about 10 wt. percent and more preferably between about 2 wt. percent and about 5 wt. percent, also expressed in terms of alkali metal oxide based on the total weight of the contact material. Preferred concentrations of sulfur are in the range of about 1 wt. percent to about 10 wt. percent and more preferably between about 2 wt. percent and about 5 wt. percent, expressed in terms of elemental sulfur based on the total weight of the contact material. The halogen is preferably present in an amount between about 1 wt. percent and about 10 wt. percent and more preferably between about 2 wt. percent and about 5 wt. percent, expressed in terms of elemental halogen based on the total weight of the contact material.

In addition to the appropriate composition, the method of preparation of the contact material is a critical factor in order to obtain an acceptable catalyst, i.e., active, selective and relatively long lived. While it is not intended to restrict the present invention to any particular form of the components or mode of operation in the reaction, it is believed that the contact material is a complex mixture of oxides of the elements contained therein, with the possible exception that sulfur and chlorine, which may be present in sulfides or chlorides, thus reducing the amount of oxygen needed to stoichiometrically balance the remainder of the components therein. Theoretically, it is also believed that the components should be in their lower states of oxidation and that some minimal concentration of halogen is necessary.

The contact materials can be prepared by any suitable method known in the art for the preparation of such mixtures in a solid form. Conventional methods include co-precipitation from an aqueous, an organic or a combination solution-dispersions, impregnation, dry mixing, wet mixing or the like, alone or in various combinations. In general any method can be used which provides contact materials containing the prescribed components in effective amounts. The contact material can be prepared by mixing the ingredients in a blender with enough water to form a thick slurry. The slurry can then be dried, usually the temperature sufficient to volatalize the water or other carrier, such as about 220° F. to about 450° F. and, thereafter, calcined, for example, at about 700° F. to about 1200° F. for from 1 to 24 hours. It is believed that the drying step, previously mentioned, results in at least some of the components being in a higher state of oxidation and, therefore, resulting in an unacceptable contact material. Consequently, it is believed that the components must be reduced to lower states of oxidation to produce an acceptable contact material. This can be accomplished in several ways.

In accordance with one mode of operation, the contact material is calcined in an oxygen free atmosphere, for example, in the presence of an inert gas, such as nitrogen, or a reducing gas, such as hydrogen, methane, ethane, etc. The mode of contacting with the oxygen free atmosphere is also believed significant. For example, it has been found that calcining the contact material in an open dish while blowing nitrogen through the furnace results in an unacceptable contact material. On the other hand, when the contact material was calcined in a closed container with nitrogen moving through the solid mass, an acceptable catalyst was obtained. Obviously, the contact material could be calcined in a vacuum but this is impractical. As an alternative, the simpler procedure of calcining in air can be carried out and the contact material placed in the reactor and pretreated with a reducing gas, such as the methane feed, in the absence of oxygen. Following the pretreatment, the methane feed and oxygen are passed through the reactor to carry out the reaction. The contact material can also be initially prepared without the halogen and, thereafter, the halogen can be supplied by pretreating the contact material in the reactor with a halogen-containing gas such as methyl chloride, methylene chloride, etc. Obviously, if the contact material is prepared by calcining in air and without halogen, the pretreatment would comprise treatment with a halogen containing gas and a reducing gas in either sequence or in combination. While work to date has not shown any significant deactivation of the contact material during the reaction, either with respect to the conversion of methane or the selectivity to higher hydrocarbons, it may, from time to time, be necessary to regenerate the contact material. As previously pointed out, a certain minimal level of chlorine on or near the surface of the contact material appears necessary and it also appears that the contact material should be in a lower state of oxidation. During use for some purposes, it has been found that the contact material deteriorates to some extent by loss of chlorine and overoxidation. To the extent that these phenomena occur, it has been found that the contact material may be reactivated or regenerated by stopping the flow of feed methane and free oxygen containing gas, passing a halogen containing gas through the contact material and, thereafter, passing a reducing gas, such as the feed methane alone, through the contact material. This treatment returns the activity and selectivity of the contact material to essentially its original condition.

Any suitable cobalt compound may be utilized in preparation of the contact material. For example, such compounds would include cobalt acetate, cobalt carbonate, cobalt nitrate, cobalt oxides and cobalt halides. Preferably, the cobalt is present in the preparation material as cobalt sulfide. However, other sulfur compounds may be used such as zirconium, cobalt, sodium, potassium, ammonium salts of sulfur, thiocyanide or thiosulfate.

Any suitable compounds of the metal selected from the group consisting of zirconium, zinc, niobium, indium, lead and bismuth may also be utilized in the preparation. Zinc compounds could include zinc acetate, zinc halides, zinc nitrate, zinc carbonate and zinc oxide. Titanium compounds can include titanium tetrachloride and titanium dioxide. Suitable zirconium compounds include zirconium tetrachloride, zirconyl nitrate, zirconyl acetate and zirconium dioxide. Niobium compounds include niobium chloride and niobium oxide. Suitable indium compounds can be utilized, such as indium chloride, indium hydroxide, indium nitrate, indium acetate and indium oxide. Lead compounds which may be utilized include lead chloride, lead nitrate, lead acetate, lead carbonate and lead oxides. Bismuth may be in the form of bismuth trichloride, bismuth nitrate, bismuth subnitrate and bismuth trioxide.

The alkali metal and phosphorous are preferably added to the preparation composition as sodium dihydrogenorthophosphate, disodiummonohydrogenorthophosphate, trisodiumorthophosphate and sodiumpyrophosphate. The alkali metal and phosphorous can be incorporated separately, utilizing sodium hydroxide, sodium carbonate, sodium bicarbonate, sodium sesquicarbonate, sodium nitrate and sodium acetate and ammonium hydrogen phosphates. As previously indicated, it is believed that the contact material is a complex mixture of oxides. Consequently, it is preferred that the starting materials be in their oxide form or in the form of compounds which, upon drying and/or calcining, are converted to oxides.

In the present invention, it has been found that the method can be carried out between two extremes, namely, low conversion of methane/high selectivity to higher hydrocarbons, particularly ethylene, and high conversion of methane/low selectivity to the higher carbons, particularly ethylene. The process parameters (space velocity, temperature, and reactant partial pressure) can, to some extent, be used to control the reaction at the desired point between these two limits. Consequently, the reaction conditions may vary between broad limits.

The volumetric ratio of methane to free oxygen should be in excess of about 1/1, preferably it is between about 1/1 and about 30/1 and still more preferably between about 4/1 and about 15/1. It has been found that a ratio of methane to free oxygen of at least about 1/1 is necessary, in accordance with the present invention, in order to obtain maximum conversion of methane and high selectivity to higher hydrocarbons, particularly ethylene.

The temperature is preferably at least about 500° C. and will generally vary between about 500° C. and about 1500° C. However, in order to obtain high conversions of methane and high selectivities to ethylene and ethane, the temperature is preferably between about 500° C. and about 900° C. and most desirably between about 600° C. and about 800° C.

It has also been found that, as the partial pressure of oxygen is increased, the selectivity to higher hydrocarbons decreases and the selectivity to carbon dioxide increases and vice versa. Total pressures may vary anywhere from around 1 atmosphere to about 1500 psi but are preferably below about 300 psi and ideally below about 100 psi.

Methane flow rates can also vary over a wide range, for example, from 0.5 to 100 cubic centimeters per minute per cubic centimeter of contact material. Preferably, however, the rate is between about 1.0 and about 75 cubic centimeters per minute per cubic centimeter of contact material.

The total flow velocities of all gaseous materials, including diluents, through a fixed bed reactor, may be at any rate effective for the oxidative conversion reaction. For example from 50 to 10,000 GHSV and preferably from 500 to 5000 GHSV.

In addition to the high conversion of methane and high selectivity to ethylene and ethane, attainable in accordance with the present invention, the contact materials are not readily poisoned and will tolerate the presence of water, carbon dioxide, carbon monoxide and the like. In addition, the contact materials appear to be long lived, with no noticeable deactivation problems. Concomitantly, the process can be carried out continuously in fixed, moving, fluidized, ebullating or entrained bed reactors.

The following examples illustrate the nature and advantages of the present invention.

In the runs of the examples, the contact materials were prepared by aqueous slurrying, drying and calcination.

The contact material was loaded in a quartz reactor having a thermocouple well centered in the contact material bed. The reactor was brought up to temperature under nitrogen or air and, thereafter, methane and air flow was begun. The gas inlet system included electronic flow measurement, a three-zone furnace for heating reactant gases and the contact material and a downstream analysis system. The reactor effluent was snap sampled, at any desired time, and analyzed for all paraffins and olefins between $C_1$ and $C_4$ and $N_2$, $O_2$, CO and $CO_2$, by gas chromatography. All contact materials are referred to in terms of weight percent of the designated element, based on the total weight of contact material.

The variables and results of this series of tests are set forth in the Table below. Conversion is mole percent of methane converted. Selectivity and yields are based on mole percent of methane feed converted to a particular product. The $CH_4$ rate can be expressed as cc/min/cc of contact material. For example, when 70 cc/min of $CH_4$ was fed to a reactor containing 20 cc of catalyst the flow rate would be 3.5 cc/min of $CH_4$/cc of contact material. The volumetric ratio of $CH_4$ to oxygen is also parenthetically given in terms of cc/min of $CH_4$ per cc/min of other gases (air) present. The Co/Zr/S/P/Na/K/Cl/O contact material was prepared by the following procedure: 107.1 g of $CoCl_2$ was dissolved in 250 mL of distilled water and 118.9 g of $Na_2S$ was dissolved in 250 ml of water. These two solutions were combined and stirred for about 20 minutes, filtered, using a Buchner funnel, the precipitate was washed in distilled water and refiltered. An aqueous slurry of the resultant CoS was formed with $Na_4P_2O_7.10H_2O$(7.5 g)Na, KOH(1.5 g), $ZrO(NO_3)_2.nH_2O$(26.7 g) and $NH_4Cl$(5.4 g). The slurry was then dried over night in a forced draft oven. The dried contact material was calcined in a quartz calcining reactor for three hours at 1500° F. in a flowing nitrogen atmosphere. The calcined contact material was then ground and sieved to 20/40 mesh.

TABLE

| Run No. | Contact Material | Volume $CH_4$/Air | Volume of Con. Mat. | Sample Time (min) | Temp (°C.) | Conversion | Selectivity % | | | | | | |
|---|---|---|---|---|---|---|---|---|---|---|---|---|---|
| | | | | | | | $C_2=$ | $C_2$ | $C_2$'s | $C_3=$ | $C_3$ | $CO_2$ | CO |
| 1 | Co/Zr/S/P/Na/K/Cl/O | 50/50 | 5 cc | 5 | 678.0 | 26.7 | 38.2 | 2.8 | 39.0 | 0.0 | 0.0 | 29.5 | 14.1 |
| | | | | 38 | 695.0 | 17.5 | 38.1 | 13.5 | 41.6 | 2.6 | 1.2 | 25.3 | 17.3 |
| | | | | 70 | 695.0 | 17.4 | 37.6 | 20.1 | 57.7 | 3.1 | 2.9 | 25.1 | 9.7 |
| | | | | 102 | 689.0 | 19.2 | 43.2 | 17.6 | 60.8 | 3.5 | 2.5 | 20.8 | 10.0 |
| | | | | 134 | 686.0 | 18.9 | 43.7 | 17.0 | 60.7 | 3.4 | 2.2 | 20.7 | 10.0 |
| | | | | 166 | 684.0 | 18.1 | 43.2 | 18.2 | 61.4 | 3.3 | 2.2 | 20.0 | 9.5 |
| 2 | $ZrO_2$ | 70/80 | 20 cc | 40 | 700.0 | 11.0 | — | — | — | — | — | 25.0 | 75.0 |
| | | | 20 cc | 40 | 700.0 | 12.0 | — | 2.5 | 2.5 | — | — | 86.0 | 11.5 |
| 3 | Quartz | 70/80 | 20 cc | 40 | 740.0 | 0.0 | — | — | — | — | — | — | — |

It has also been found that the production of $CO_2$ was high and, hence, the HC selectivity was low, if the concentration of $O_2$ in the initial feed stream is high. Accordingly, the HC selectivity can be increased and the $CO_2$ production concomittantly decreased by staged addition of the free oxygen containing gas to provide an effective portion of the total $O_2$ at a plurality of spaced points along a continuous contact material bed or between separate contact material beds.

While specific materials, conditions of operation, modes of operation and equipment have been referred to herein, it is to be recognized that these and other specific recitals are for illustrative purposes and to set forth the best mode only and are not to be considered limiting.

What is claimed is:

1. A method for the oxidative conversion of methane to higher hydrocarbons, comprising:
   contacting a feed material comprising methane with a solid contact material, comprising:
   cobalt; at least one metal selected from the group consisting of zirconium, zinc, niobium, indium, lead and bismuth; phosphorous; at least one Group IA metal; and oxygen, under oxidative conversion conditions sufficient to convert said methane to said higher hydrocarbons.

2. A method in accordance with claim 1 wherein the feed material is natural gas.

3. A method in accordance with claim 1 wherein the metal selected from the group consisting of zirconium, zinc, niobium, indium, lead and bismuth is zirconium.

4. A method in accordance with claim 1 wherein the Group IA metal is sodium.

5. A method in accordance with claim 1 wherein the contact material is prepared by:
   combining compounds of the elements; and calcining the thus combined compounds in an oxygen free atmosphere.

6. A method in accordance with claim 1 wherein the contact material is prepared by:
combining compounds of the elements;
calcining the thus combined compounds in the presence of a free oxygen-containing gas;
placing the thus calcined contact material in a reaction zone;
pretreating the contact material by passing a reducing gas through the contact material in said reaction zone and, thereafter;
passing the feed material through the contact material.

7. A method in accordance with claim 6 wherein the reducing gas is methane.

8. A method in accordance with claim 1 wherein the temperature of contacting is at least about 500° C.

9. A method in accordance with claim 1 wherein the temperature of contacting is between about 500° C. and 1500° C.

10. A method in accordance with claim 1 wherein the contact material further comprises at least one material selected from the group consisting of a halogen and sulfur.

11. A method in accordance with claim 10 wherein the contact material further comprises chlorine.

12. A method in accordance with claim 1 wherein the contact material additionally contains potassium.

13. A method in accordance with claim 10 wherein the contact material further comprises sulfur.

14. A method in accordance with claim 10 wherein the contact material further comprises both chlorine and sulfur.

15. A method in accordance with claim 10 wherein the contact material further comprises both a halogen and sulfur.

16. A method in accordance with claim 10 wherein the contact material further comprises a halogen.

17. A method in accordance with claim 13 wherein the feed material is contacted with the contact material in the presence of a free oxygen containing gas.

18. A method in accordance with claim 17 wherein the method is carried out in an essentially continuous manner.

19. A method in accordance in the claim 17 wherein the volumetric ratio of methane to free oxygen is at least about 1/1.

20. A method in accordance with claim 17 wherein the volumetric ratio of methane to free oxygen is between about 1/1 and about 30/1.

* * * * *